US00PP29948P3

(12) United States Plant Patent
Snijder

(10) Patent No.: US PP29,948 P3
(45) Date of Patent: Dec. 4, 2018

(54) ***PELARGONIUM* PLANT NAMED 'PEQZ0013'**

(50) Latin Name: *Pelargonium interspecific*
Varietal Denomination: PEQZ0013

(71) Applicant: SYNGENTA PARTICIPATIONS AG, Basel (CH)

(72) Inventor: Ronald Christiaan Snijder, Andijk (NL)

(73) Assignee: Syngenta Participations AG, Basel (CH)

( * ) Notice: Subject to any disclaimer, the term of this patent is extended or adjusted under 35 U.S.C. 154(b) by 29 days.

(21) Appl. No.: 15/330,756

(22) Filed: Nov. 3, 2016

(65) Prior Publication Data

US 2017/0359936 P1 Dec. 14, 2017

(51) Int. Cl.
*A01H 6/42* (2018.01)
*A01H 5/02* (2018.01)

(52) U.S. Cl.
USPC ..... Plt./324
CPC ..... *A01H 6/42* (2018.05); *A01H 5/02* (2013.01)

(58) Field of Classification Search
USPC ..... Plt./324
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0013' particularly distinguished by the bright white colored inflorescences held above the dark green foliage, very heat and drought tolerant with continuous color through the most extreme summer heat, and on a semi-trailing plant with semi double flowers.

1 Drawing Sheet

Latin name of the genus and species of the plant claimed: *Pelargonium interspecific.*

Varietal denomination: 'PEQZ0013'.

BACKGROUND OF THE NEW PLANT

The present invention comprises a new *Pelargonium*, botanically known as *Pelargonium interspecific*, and hereinafter referred to by the variety name 'PEQZ0013'.

'PEQZ0013' is a product of a planned breeding program. The new cultivar 'PEQZ0013' has bright white colored inflorescences held above dark green foliage, very heat and drought tolerant with continuous color through the most extreme summer heat on a semi-trailing plant with semi double flowers.

'PEQZ0013' originates from a cross-pollination in a controlled breeding program made in April 2010, in a greenhouse in Enkhuizen, The Netherlands. The female parent was a more heat sensitive unpatented proprietary plant of *P. peltatum* x *P.* x *hortorum* parentage 'PEZ-AA5008-10'. The male parent of 'PEQZ0013' was a taller plant of *P.* x *hortorum* descent 'PEZ-AN2018-01'. The resultant seed was sown in December 2010.

'PEQZ0013' was selected as one flowering plant within the progeny of the stated cross in April 2011 in a greenhouse in Enkhuizen, The Netherlands.

The first act of asexual reproduction of 'PEQZ0013' was accomplished when vegetative cuttings were propagated from the initial selection in May 2011 in a greenhouse in Enkhuizen, The Netherlands.

BRIEF SUMMARY OF INVENTION

Horticultural examination of plants grown from cuttings of the plant initiated in May 2011 in Enkhuizen, The Netherlands, and continuing thereafter, has demonstrated that the combination of characteristics as herein disclosed for 'PEQZ0013' are firmly fixed and are retained through successive generations of asexual reproduction.

'PEQZ0013' has not been observed under all possible environmental conditions. The phenotype may vary significantly with variations in environment such as temperature, light intensity, and day length.

A Plant Breeder's Right for this cultivar was applied for in the European Union on Jun. 13, 2016, No. 2016/1415. 'PEQZ0013' has not been made publicly available prior to the effective filing date of this application, notwithstanding any disclosure that may have been made less than one year prior to the effective filing date of this application by the inventor or another who obtained 'PEQZ0013' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawing shows typical flower and foliage characteristics of 'PEQZ0013' with colors being as true as possible with an illustration of this type.

Figure 1:
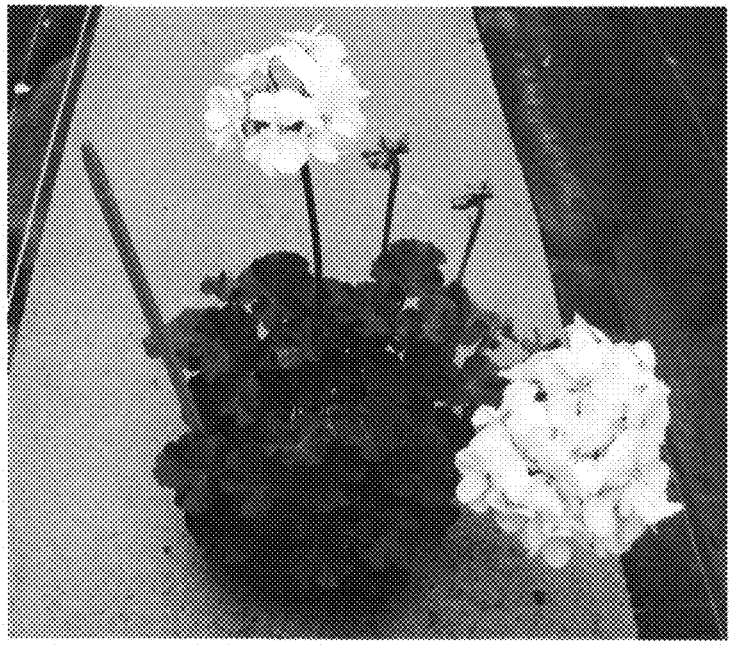
Figure 2:
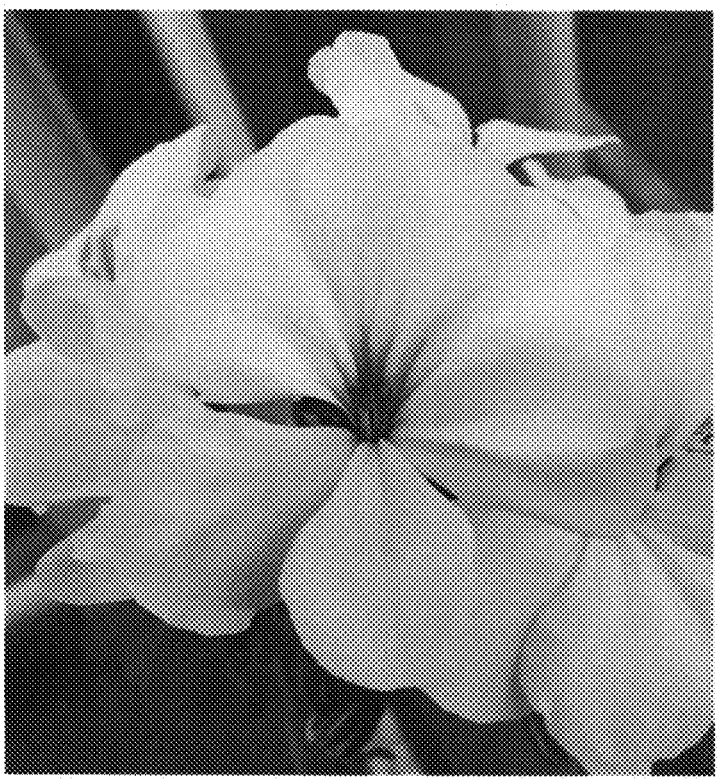

The photographic drawings show in FIG. 1, 1 flowering plant of the new variety and in FIG. 2, a close-up of an inflorescence.

DETAILED BOTANICAL DESCRIPTION

The plant descriptions and measurements were taken in Enkhuizen, The Netherlands in late September 2016 under natural light. These plants were 18 weeks old and were grown in a 15 cm pot, in a greenhouse trial. From these plants, one plant is shown on the photographs. The photographs were taken in October 2016.

Color references are made to The Royal Horticultural Society Colour Chart (R.H.S.) 2001.

TABLE 1

DIFFERENCES BETWEEN THE NEW VARIETY 'PEQZ0013' AND A MOST SIMILAR VARIETY

| | 'PEQZ0013' | 'Zonfiwie' (U.S. Plant Patent No. 21,188) |
|---|---|---|
| Plant shape: | Spreading to Semi-trailing | Mounding |
| Anther color: | Orange red (RHS 35B) | Light orange red (RHS 32D) |
| Stigma color: | Light pink (RHS 65B) | White (RHS 157D) |

Plant:

*Form, growth and habit.*—Spreading, semi-trailing habit, heat and drought tolerant with continuous color through the most extreme summer heat.

*Plant height.*—12-14 cm.

*Plant height (inflorescence included).*—14-24 cm.

*Plant width.*—21-27 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B.

Foliage:

*Immature leaf, color upper surface.*—Between RHS 143B and RHS 141A.

*Immature leaf, lower surface.*—Closest to RHS 139B.

*Mature leaf, color upper surface.*—Between RHS 137A and RHS 139A.

*Mature leaf, color lower surface.*—Between RHS 137C and RHS 138B.

*Length.*—6-7 cm.

*Width.*—7-8.5 cm.

*Shape.*—Cordate.

*Base shape.*—Cordate.

*Apex shape.*—Acute.

*Margin.*—Slightly dentate, slightly crenate.

*Texture upper side.*—Hirsute.

*Texture lower side.*—Hirsute.

*Leaf zonation color.*—None.

*Color of veins, upper surface.*—RHS 146C at base of leaf.

*Color of veins, lower surface.*—RHS 145C.

*Pattern of veining.*—Palmate.

*Petiole color.*—RHS 137C.

*Petiole length.*—4-7 cm.

*Diameter of petiole.*—0.2-0.4 cm.

*Texture.*—Pilose, hirsute, glandular hairs.

Stem:

*Quantity of branches.*—3-5.

*Color of stem.*—RHS 144B.

*Length of stem.*—6-18 cm.

*Diameter.*—0.5-0.6 cm.

*Length of internodes.*—2-2.5 cm.

*Texture.*—Sparsely hirsute, pilose, glandular hairs.

Peduncle:

*Color of peduncle.*—RHS 144A.

*Length of peduncle.*—13-19 cm.

*Peduncle diameter.*—0.3-0.4 cm.

*Texture.*—Hirsute, glandular hairs.

Pedicel:

*Color of pedicel.*—RHS 144A aging to purple (RHS N79).

*Length of pedicel.*—3.5-4.1 cm.

*Diameter of pedicel.*—0.15-0.2 cm.

*Texture.*—Sparsely pilose, glandular hairs.

Bud (just before opening):

*Color.*—Closest to RHS 157A.

*Length.*—2-2.5 cm.

*Width.*—0.7-0.9 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—4, with 5 immature umbels in various stages.

*Fragrance.*—None.

*Umbel diameter.*—11-12 cm.

*Umbel depth.*—7-9 cm.

Corolla:

*Form.*—Semi-double.

*Number of petals.*—7-8.

*Diameter of flower.*—5-6 cm.

*Depth of flower.*—1.5-2 cm.

*Color upper petals, upper surface.*—RHS N155B with red-purple (RHS 65A) veins at base.

*Color upper petals, lower surface.*—RHS N155A.

*Length of upper petals.*—2.5-3.2 cm.

*Width of upper petals.*—1.8-2.1 cm.

*Color lower petals, upper surface.*—RHS N155B.

*Color lower petals, lower surface.*—RHS N155A.

*Length of lower petals.*—2.5-2.7 cm.

*Width of lower petals.*—2.1-2.3 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—6-7.

*Color of sepals.*—RHS 144 A with purple (N79) mottling.

*Length of sepals.*—1.2-1.3 cm.

*Width of sepals.*—0.2-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.2 cm.

*Style color.*—RHS 43C.

*Style length.*—0.5-0.7 cm.

*Stigma color.*—RHS 42A.

*Ovary color.*—RHS 144D.

*Ovary length.*—0.3-0.4 cm.

*Ovary diameter.*—0.2 cm.

Androecium:

*Number of stamens.*—7.

*Color of filaments.*—RHS 43C at the tip, RHS 155C at the base.
*Length filaments.*—0.7 cm.
*Anther color.*—RHS 70A.
*Length of anthers.*—0.2 cm.
*Color of pollen.*—RHS 34C.
*Pollen amount.*—Moderate.
*Fertility/seed set.*—Has not been determined to date.
*Disease/pest resistance.*—Has not been determined to date.

What is claimed is:

1. A new and distinct variety of *Pelargonium* plant named 'PEQZ0013' substantially as illustrated and described herein.

* * * * *